United States Patent [19]
Wilson

[11] Patent Number: 5,144,947
[45] Date of Patent: Sep. 8, 1992

[54] APPARATUS AND METHOD FOR ANTITACHYCARDIA PACING IN A ARRHYTHMIA CONTROL SYSTEMS

[75] Inventor: Stephen G. Wilson, Stanmore, Australia

[73] Assignee: Telectronics Pacing Systems, Inc., Englewood, Colo.

[21] Appl. No.: 673,900

[22] Filed: Mar. 22, 1991

[30] Foreign Application Priority Data

Apr. 3, 1990 [AU] Australia ................................ PJ9437

[51] Int. Cl.$^5$ ............................................. A61N 1/36
[52] U.S. Cl. .............................................. 128/419 PG
[58] Field of Search ................................. 128/419 PG

[56] References Cited

U.S. PATENT DOCUMENTS

| | | | |
|---|---|---|---|
| 3,857,398 | 12/1974 | Rubin | 128/419 D |
| 3,942,534 | 3/1976 | Allen et al. | 128/419 PG |
| 4,390,021 | 6/1983 | Spurrell | 128/419 PG |
| 4,398,536 | 8/1983 | Nappholz et al. | 128/419 PG |
| 4,406,287 | 9/1983 | Nappholz et al. | 128/419 PG |
| 4,408,606 | 10/1983 | Spurrell et al. | 128/419 PG |
| 4,541,430 | 9/1985 | Elmqvist et al. | 127/419 PG |
| 4,574,437 | 3/1986 | Segerstad et al. | 128/419 PG |
| 4,875,483 | 10/1989 | Vollmann et al. | 128/419 PG |
| 4,940,054 | 7/1990 | Grevis et al. | 128/419 PG |
| 5,103,822 | 4/1992 | Duncan | 128/419 PG |

Primary Examiner—William E. Kamm
Assistant Examiner—J. Jastrzab
Attorney, Agent, or Firm—Gottlieb, Rackman & Reisman

[57] ABSTRACT

A method and apparatus for treating tachycardias are disclosed which utilize tachycardia cycle lengths in connection with selecting the type of antitachycardia pacing to be used in such treatment. A range of tachycardia cycle lengths is selected for which antitachycardia pacing treatment is indicated. This range is divided into a plurality of sub-ranges of tachycardia cycle lengths, and corresponding storage locations are established for each of the tachycardia cycle length sub-ranges. Antitachycardia pacing parameters which have been successful in reverting previous tachycardias are stored in their corresponding storage locations, and subsequent tachycardias are treated using antitachycardia pacing parameters selected from storage locations that correspond to, or are closest to correspondence with, the storage locations corresponding to the tachycardias to be treated.

23 Claims, 6 Drawing Sheets

APPARATUS AND METHOD FOR ANTITACHYCARDIA PACING IN A ARRHYTHMIA CONTROL SYSTEMS

TECHNICAL FIELD

This invention relates to implantable medical devices which monitor the cardiac state of a patient by sensing the patient's intrinsic rhythm, ventricular tachycardia and ventricular fibrillation/flutter, and which deliver therapy in the form of electrical energy to cardiac tissue in an attempt to revert tachycardia and restore a normal sinus rhythm.

BACKGROUND OF THE INVENTION

As used herein, the term tachycardia refers to any fast abnormal rhythm of the heart which may be amenable to treatment by electrical discharges and specifically includes supraventricular tachycardia (SVT), ventricular tachycardia (VT), and ventricular flutter and ventricular fibrillation (VF).

The term cardioversion refers to the discharge of electrical energy into cardiac tissue in an attempt to terminate or revert a tachycardia. It may range from a high (40 Joules or more) to a low (less than 1 Joule) energy discharge. The discharge may be monophasic or biphasic but is not restricted to these waveforms. Cardioversion shocks may or may not be synchronized to the rhythm of the heart. Defibrillation is a particular example of cardioversion.

This invention applies equally to devices which deliver energy synchronized to an R-wave and to those that do not, and it applies to devices which use lower energy pulses (up to 1 Joule) as well as to devices which use greater energy pulses (up to 40 Joules or more). The invention applies to devices which deliver cardioverting shocks alone as well as in combination with antitachycardia pacing pulses.

U.S. Pat. No. 3,857,398 to Rubin describes a combined pacer/defibrillator. This device either performs a bradycardia pacing or a defibrillation function depending on the condition detected. If a VT/VF is detected, the device is switched to the defibrillating mode. After a period of time to charge a capacitor, a defibrillation shock is delivered to the patient.

A multiprogrammable, telemetric, implantable defibrillator is disclosed in the co-pending patent application of N. L. Gilli et , Ser. No. 239,624, filed Sep. 1, 1988 now abandoned, and entitled "Reconfirmation Prior to Shock in Implantable Defibrillator". The Gilli et al. device contains a bradycardia support system as well as a high energy shock system to revert ventricular tachycardias to normal sinus rhythm. On reconfirmation of the presence of a tachycardia, a shock is delivered to the patient, either at a predetermined time or when the desired energy level is reached.

A further development in the field of combined implantable devices is described in U.S. Pat. No. 4,940,054 to Grevis and Gilli, which issued on Jul. 10, 1990, and is entitled "Apparatus and Method for Controlling Multiple Sensitivities in Arrhythmia Control Systems Including Post Therapy Pacing Delay". This device is a microcomputer-based arrhythmia control system which is programmable by means of a telemetric link. The device provides single chamber bradycardia support pacing, antitachycardia pacing, and cardioversion or defibrillation shocks for restoring normal sinus rhythm to a patient.

Various developments have been made in tachycardia control pacers. Tachycardia is a condition in which the heart beats very rapidly, typically above 150 beats per minute (hereinafter "bpm"). There are several different pacing modalities which have been suggested for the termination of tachycardia. The underlying principle in all of them is that if a pacer stimulates the heart at least once shortly after a heartbeat, before the next naturally occurring heartbeat at the rapid rate, the heart may successfully revert to normal sinus rhythm. Tachycardia is often the result of electrical feedback within the heart. A natural beat results in the feedback of an electrical stimulus which prematurely triggers another beat. By interposing a stimulated heartbeat, the stability of the feedback loop is disrupted.

In U.S. Pat. No. 3,942,534 to K. R. Allen et al., which issued on Mar. 9, 1976, and is entitled "Device For Terminating Tachycardia," there is disclosed a pacer which, following detection of a tachycardia, generates an atrial (or ventricular) stimulus after a delay interval. If that stimulus is not successful in terminating the condition, then another stimulus is generated after another premature heartbeat following a slightly different delay. The device constantly adjusts the delay interval by scanning through a predetermined delay range. Stimulation ceases as soon as the heart is restored to sinus rhythm. If successful reversion is not achieved during one complete scan, then the cycle is repeated. The device further provides a second stimulus following the first, both stimuli occurring within the same tachycardia cycle, i.e. before the next naturally occurring rapid beat. The time period between a heartbeat and the first stimulus is known as the initial delay, while the time period between the first stimulus and the second stimulus is known as the coupled interval. In the above device, once the coupled interval is set by a physician it is fixed, and therefore the second stimulus always occurs a predetermined time after the first stimulus, no matter when the first stimulus occurs after the last heartbeat.

U.S. Pat. No. 4,390,021 to R. A. J. Spurrell et al., which issued on Jun. 28, 1983, and is entitled "Two Pulse Tachycardia Control Pacer," discloses a pacer for controlling tachycardia in which the coupled interval is scanned in addition to the initial delay. The time parameters which are successful in terminating the tachycardia is stored so that upon confirmation of another tachycardia event, the previously successful time parameters are the first ones to be tried. The device also allows tachycardia to be induced by the physician to allow for programming of the initial delay and the coupled interval parameters.

U.S. Pat. No. 4,398,536 to T. A. Nappholz et al., which issued on Aug. 16, 1983, discloses a scanning burst tachycardia control pacer. Following each tachycardia confirmation, a burst of a programmed number of stimulating atrial (or ventricular) pulses is generated. The rates of the bursts increase from cycle to cycle whereby following each tachycardia confirmation, a pulse burst at a different rate is generated. The rate of a burst which is successful in terminating tachycardia is stored, and following the next tachycardia confirmation, the stored rate is used for the first burst which is generated.

U.S. Pat. No. 4,406,287 to T. A. Nappholz et al., which issued on Sep. 27, 1983, discloses a variable length scanning burst tachycardia control pacer. The physician programs the maximum number of pulses in a burst. The number of pulses in a burst is scanned, and the number which is successful in terminating tachycardia is registered so that it is available for first use when a new tachycardia episode is confirmed. Successive bursts, all at the same rate, have different numbers of pulses, the pulse number scanning being in the upward direction. If all bursts are unsuccessful, a new rate is tried and the number scanning begins over again. Thus all combinations of rates and pulse numbers are tried, with the successful combination being used first following the next tachycardia confirmation.

U.S. Pat. No. 4,408,606 to R. A. J. Spurrell et al., which issued on Oct. 11, 1983 discloses a rate related tachycardia control pacer. Following tachycardia confirmation, a burst of at least three stimulating pulses is generated. The time intervals between successive pulses decrease by a fixed decrement; hence the rate of the pulses increases during each cycle of operation. The first pulse is generated following the last heartbeat which is used to confirm tachycardia, at a time which is dependent on the tachycardia rate. The time delay between the last heartbeat and the first pulse in the burst is equal to the time interval between the last two heartbeats less the fixed decrement which characterizes successive time intervals between stimulating pulses.

The problem with the storage of successful antitachycardia pacing parameters as described by Spurrell et al. U.S. Pat. No. 4,390,021, Nappholz et al. U.S. Pat. No. 4,398,536, Nappholz et al. U.S. Pat. No. 4,406,287 and Spurrell al. U.S. Pat. No. 4,408,606 is that a subsequent episode of tachyarrhythmia may be triggered in a different circuit from that in which a previous episode was pace-terminated. Accordingly, the recalled parameters will not necessarily be appropriate for the new tachyarrhythmia.

Depending on the relative differences in circuit path length as well as the direction of scanning, it may be that starting from inappropriate recalled parameters will cause even more pacing trains to be taken to reach reversion than would be the case if scanning had been started from zero.

Commonly, a patient will have more than one triggerable reentrant circuit. It is an object of the present invention to discriminate between different reentrant circuits and to associate different stored sets of successful antitachycardia pacing parameters with different circuits.

SUMMARY OF THE INVENTION

Antitachyarrhythmia pacing (ATP) is generally restricted to rhythms having tachycardia cycle lengths (TCL) lying between two extremes. As used herein, the extremes are referred to as the Maximum Tachycardia Cycle Length for ATP (TCLmax) and the Minimum Tachycardia Cycle Length for ATP (TCLmin). In the disclosed invention, the range of cycle lengths over which antitachycardia pacing may be applied is partitioned into a given number of sub-ranges. Once a combination of antitachycardia pacing parameters has been established by scanning to be successful in terminating a tachycardia, the cycle length sub-range in which that tachycardia is situated is calculated, and the scanning parameters are stored in storage locations or bins in such a way as to be identifiable by the corresponding location or bin number.

It is preferable that the bin number under which a set of successful parameters is stored should be that for the tachycardia cycle length at the last reconfirmation prior to reversion. However, it may alternately be that for the cycle length of the tachycardia when first it was detected. The choice may be programmed by the physician.

It is also preferable that, for a particular cycle length bin, if a newly successful pacing train is found to have a different scanning parameter value from that of an earlier successful train, the old value is discarded and the new value is stored in association with the bin.

The overwriting of old successful scanning values is based on the principle that, over time, a patient's cardiac depolarization conduction velocity can change, due to the influence of drugs and other factors. Thus, the timing characteristics needed of a pacing train to revert an arrhythmia triggered in a particular reentrant circuit can also change over time. Therefore, it is appropriate that the stored successful scanning parameter value in any given tachycardia cycle length bin is that for the most recently applied successful pacing train.

The principle of the invention disclosed applies equally to any type of parameter scanned in antitachyarrhythmia pacing, be it for example the initial or coupled delays, or the length of the train, or any combination of these or other parameters.

The principle of the invention disclosed applies equally to antitachycardia pacing algorithms with any number of scanning parameters. If more than one parameter is scanned in the algorithm in use, each parameter's value for a successful pacing train is stored in association with the tachyarrhythmia's cycle length bin.

For simplicity, the descriptions here generally assume that the antitachycardia pacing algorithm in use has just one scanning parameter.

BRIEF DESCRIPTION OF THE DRAWINGS

While the specification concludes with claims particularly pointing out and distinctly claiming the subject matter regarded as the invention herein, it is believed that the present invention will be more readily understood from the following description, taken in conjunction with the accompanying drawings, in which:

DETAILED DESCRIPTION OF THE INVENTION

Figure 1:
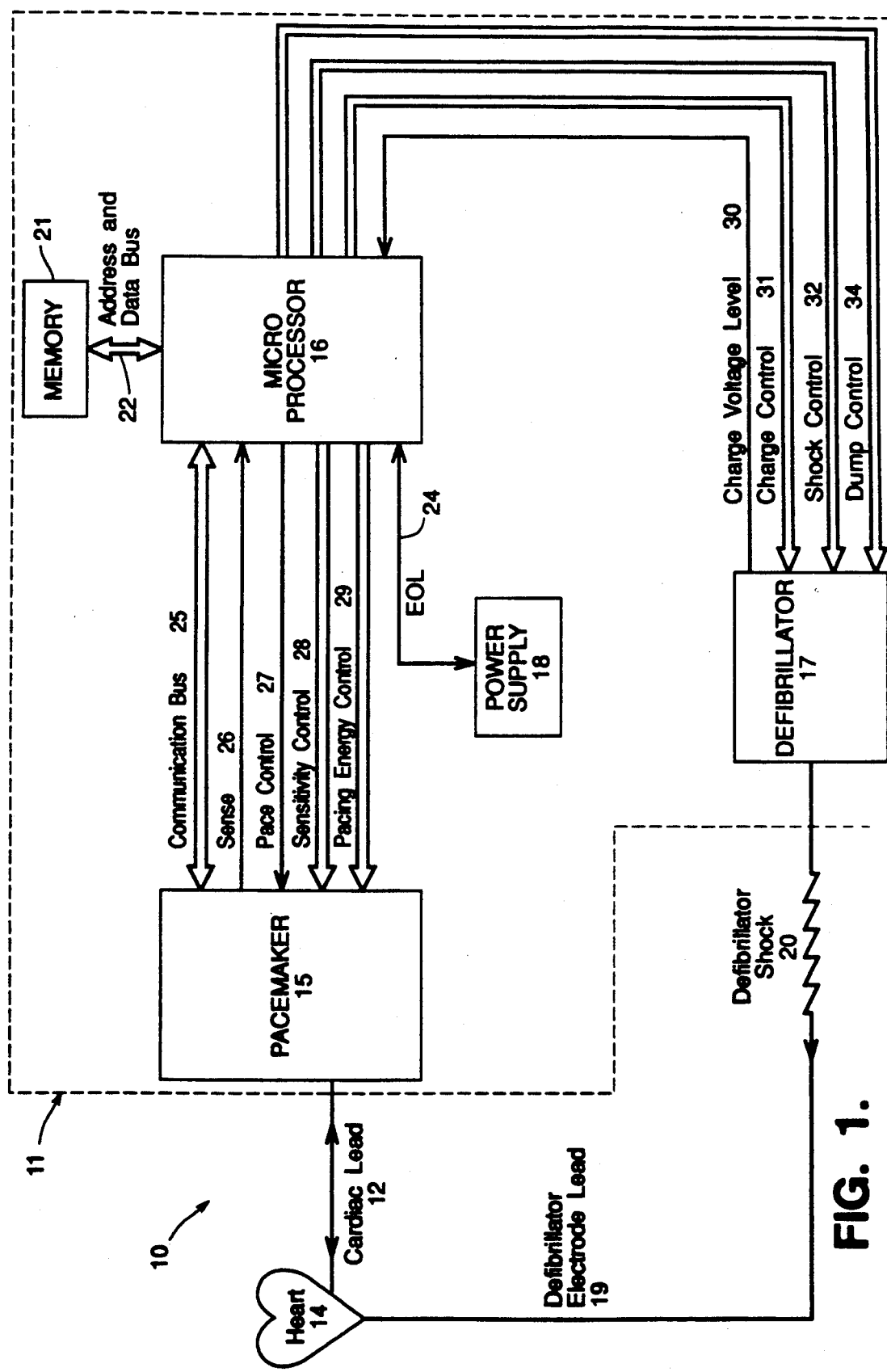
FIG. 1 depicts a block diagram of an arrhythmia control system in accordance with one embodiment of the invention.

Referring to FIG. 1, there is depicted a block diagram of an arrhythmia control system 10. System 10 is designed to be implantable and includes a pulse module 11 and appropriate leads. More particularly, system 10 will generally include a cardiac lead or leads 12 extending to a patient's heart 14 for the administration of therapy to the atrium or ventricle, or to both, of the patient's heart for the administration of therapy thereto. System 10 generally also includes a pacemaker 15 for the detection of analog signals representing cardiac electrical activity and for the delivery of pacing pulses to the heart; a microprocessor 16 which, in response to various inputs received from the pacemaker 15 as well as from a defibrillator 17, performs various operations so as to generate different control and data outputs to both pacemaker 15 and defibrillator 17; and a power supply 18 for the provision of a reliable voltage level to pacemaker 15, microprocessor 16 and defibrillator 17 by suitable electrical conductors (not shown). Defibrillator 17 produces a high voltage to charge its capacitors (not shown) and then discharges the capacitors in response to control signals from microprocessor 16. A defibrillator electrode lead 19 transfers the energy of a defibrillator shock 20 from the implanted pulse module 11 to the surface of the heart 14.

Microprocessor 16 is connected to an external memory 21 by an address and data bus 22. An end-of-life (EOL) signal line 24 is used to provide, to microprocessor 16, a logic signal indicative of the approach of battery failure in power supply 18.

As more fully described below, microprocessor 16 and pacemaker 15 are connected by a communication bus 25, a sense line 26, a pace control line 27, a sensitivity control bus 28, and a pacing energy control bus 29. As also more fully described below, microprocessor 16 is connected to defibrillator 17 by a charge voltage level line 30, a charge control bus 31, a shock control bus 32, and a dump control bus 34.

Figure 2:
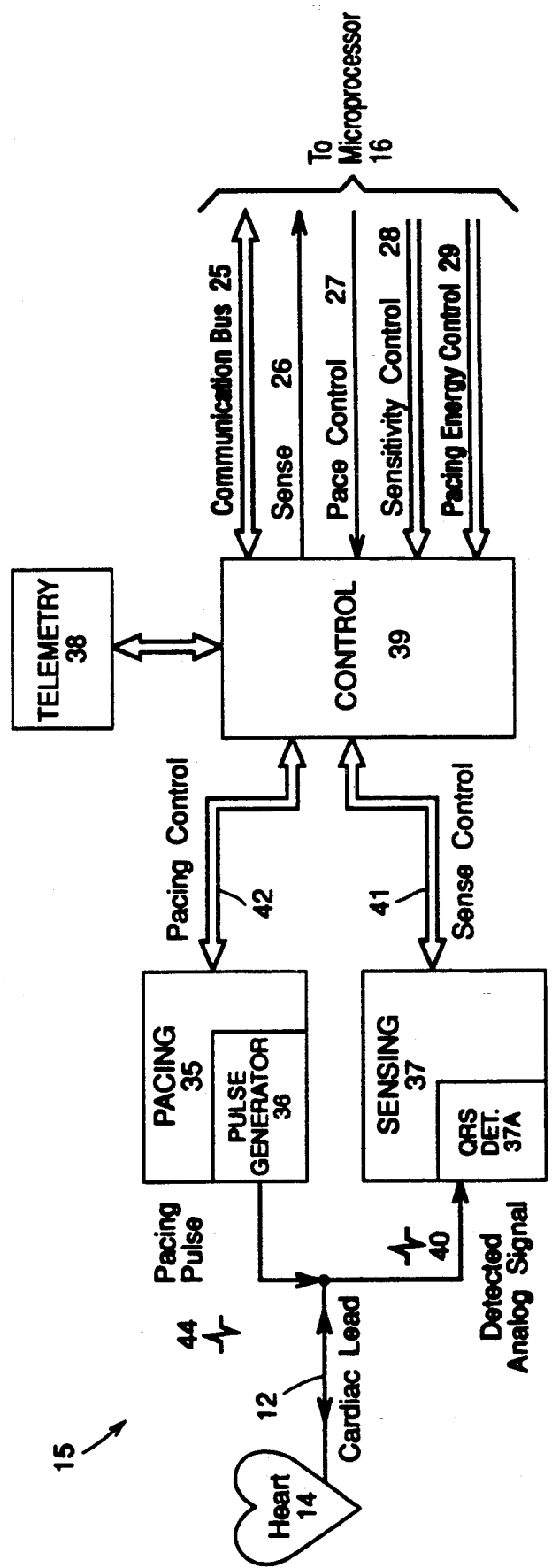
FIG. 2 depicts a block diagram of a pacemaker utilized in the system of FIG. 1.

Referring to FIG. 2, pacemaker 15 comprises a pacing circuit 35 which includes a pacing pulse generator 36, a sensing circuit 37, and a telemetry circuit 38. In addition, there is a control block 39 which includes an interface to microprocessor 16.

In operation, sensing circuit 37 detects analog signals 40 from the heart 14 in an internal QRS detector 37A and converts the detected signals to digital signals. Furthermore, sensing circuit 37 receives an input sense control signal (which determines the sensitivity of the detection circuits in sensing circuit 37) by way of a sense control bus 41 from control block 39. As more fully described below, a change in this sensitivity will affect the voltage deviation required at the sensing electrode for a sense to be registered.

Pacing circuit 35 also receives inputs from control block 39, including a pace control and a pacing energy control, by way of pacing control bus 42, which carries the signals that arrive at block 39 via pace control line 27 and pacing energy control bus 29. The pace control determines the type of pacing to occur while the magnitude of the pulse energy is determined by the pacing energy control. Pacing circuit 35 causes pulse generator 36 to generate pacing pulses 44 which are delivered to the patient's heart 14 by means of cardiac lead 12.

Telemetry circuit 38 provides a bi-directional link between control block 39 of pacemaker 15 and an external device such as a programmer (not shown). It allows data such as the operating parameters to be read from or altered in the implanted pulse module 11 (FIG. 1).

Figure 3:
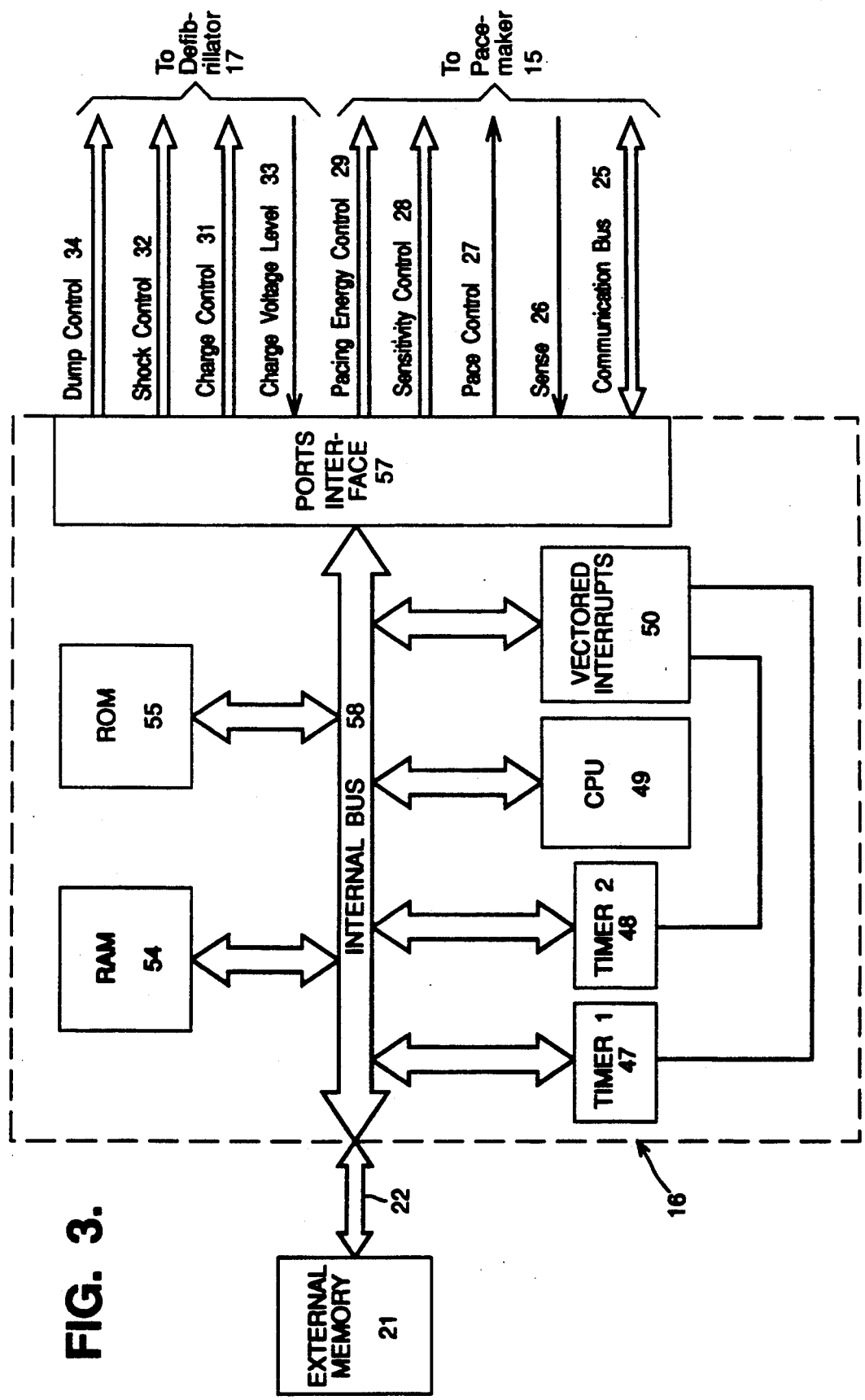
FIG. 3 depicts a block diagram of a microprocessor utilized in the system of FIG. 1.

Referring to FIG. 3, microprocessor 16 comprises two 16-bit timers 47 and 48, a central processing unit or CPU 49, a vectored interrupts block 50, a random access memory or RAM 54, a read only memory or ROM 55, a ports interface 57 and an internal communications bus 58. RAM 54 acts as a scratch pad and active memory during execution of the various programs stored in ROM 55 and used by microprocessor 16. These programs include system supervisory programs, detection algorithms for detecting various arrhythmias, and programming implementing the logic flow diagram of FIG. 4, as well as storage programs for storing, in external memory 21, data concerning the functioning of module 11 and the electrogram provided by cardiac lead 12 (FIG. 1). Timers 47 and 48 and associated control software implement some timing functions required by microprocessor 16 without resort entirely to software, thus reducing computational loads on and power dissipation by CPU 49.

Signals received from telemetry circuit 38 (FIG. 2) permit an external programmer (not shown) to change the operating parameters of pacemaker 15 by supplying appropriate signals to control block 39. Communications bus 25 (FIG. 3) serves to provide signals indicative of such control to microprocessor 16. Thus, it is also possible for an external programmer to control operation of defibrillator 17 (FIG. 1) by means of signals provided to microprocessor 16.

Appropriate telemetry commands may cause telemetry circuit 38 (FIG. 2) to transmit data to the external programmer. Data stored is read out, by microprocessor 16, on to communications bus 25, through control block 39 in pacemaker 15, and into telemetry circuit 38 for transmission to the external programmer by a transmitter in telemetry circuit 38.

Microprocessor 16 (FIG. 3) receives various status and/or control inputs from pacemaker 15 and defibrillator 17. During normal pacer operations the input signal to pacemaker 15 is a sense signal on sense line 26 which is used by microprocessor 16 to perform operations such as arrhythmia detection. Microprocessor 16 produces outputs such as the pace control on pace control line 27 which determines the type of pacing to take place.

Other pacemaker control outputs generated by microprocessor 16 include a pacing energy control signal on pacing energy control bus 29 which determines the magnitude of the pulse energy, and a sensitivity control signal on sensitivity control bus 28, which determines the sensitivity setting of the sensing circuit 37.

Microprocessor 16 provides to defibrillator 17 a shock control signal on shock control bus 32 which indicates that a shock is to be delivered to the patient, a dump control signal on dump control bus 34 which indicates that a shock is to be dumped at an internal load within defibrillator 17, and a charge control signal on charge control bus 31 which determines the voltage level of the shock to be delivered. Charge voltage level line 33 provides a digital signal representative of charge voltage from an analog to digital converter within defibrillator 17, thus providing a feedback loop which assures that a shock of proper energy level is delivered by defibrillator 17.

Figure 4:
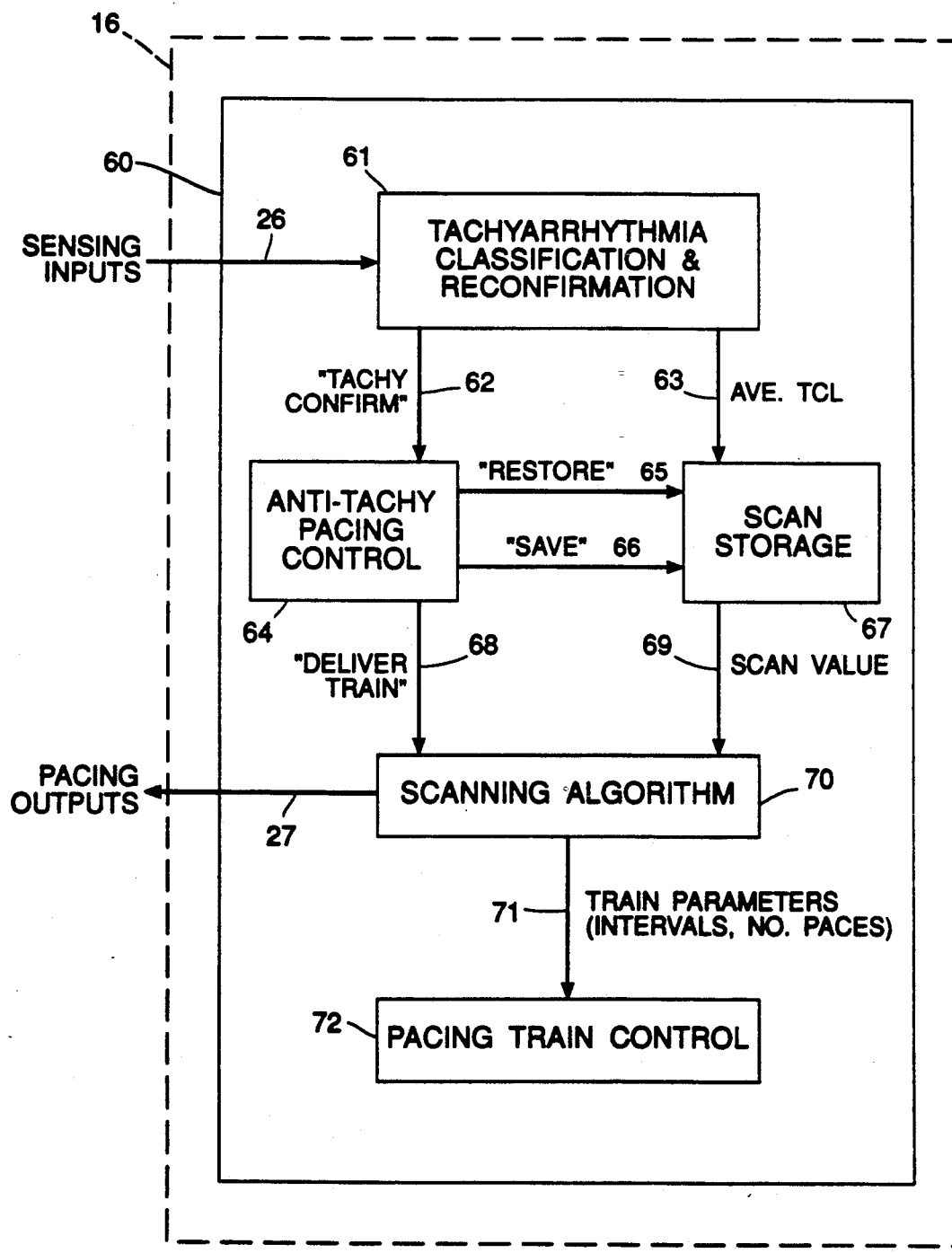
FIG. 4 is a logic flow diagram which depicts the modular decomposition of antitachyarrhythmia pacing software within the microprocessor of FIG. 1.

Referring to FIG. 4, there is illustrated a logic flow diagram which depicts generally at 60 the modular decomposition of the antitachyarrhythmia pacing software within the microprocessor 16 of FIG. 1. Sensing inputs are delivered to the software via sensing line 26. Tachyarrhythmia classification and reconfirmation are provided by software at block 61. If a tachyarrhythmia is detected and reconfirmed, a "tachy confirm" signal 62 passes to an antitachycardia pacing control block 64. At the same time, a signal 63, representing the average tachycardia cycle length of the reconfirmed tachyarrhythmia, is sent to a scan storage block 67. From pacing control block 64, either a "restore" signal 65 or a "save" signal 66 passes to scan storage block 67, which interchanges a scan value 69 with a scanning algorithm block 70. A "deliver train" signal 68 passes from antitachycardia pacing control block 64 to a scanning algorithm block 70. From scanning algorithm block 70, a train parameters signal 71 passes to a pacing train control block 72, which issues pacing outputs to the patient via pace control line 27.

In the preferred embodiment of the invention, tachycardia cycle lengths are measured to a resolution of 4 milliseconds and are represented internally in multiples of 4 milliseconds. Thus, one byte with a numerical range of 0 to 255 can represent cycle lengths from 0 to 1020 milliseconds. The device thereby limits the minimum tachycardia cycle length (TCLmin) to greater than or equal to 0 milliseconds, and limits the maximum tachycardia cycle length (TCLmax) to less than or equal to 1020 milliseconds. The actual values of TCLmin and TCLmax are programmed by the physician in accordance with the principles of antitachycardia pacing.

The partitioning of tachycardia cycle lengths is achieved by the inherent resolution of the measured tachycardia cycle length. An array of 256 additional storage location units or bins is used to store the scanning parameter for each successful reversion by pacing. Thus, a corresponding scanning parameter value can be stored for each unique, tachycardia reverting, cycle length value.

After detection and reconfirmation of a tachyarrhythmia, the invention examines or indexes the contents of the scanning parameter storage array to arrive at the confirmed tachycardia cycle length bin. If there is a stored scanning parameter value for that cycle length, it is recalled and scanning is commenced at that value. If not, the array is searched both upwards and downwards until a filled cycle length bin is found. The stored scanning parameter value for the cycle length which is numerically closest to the newly confirmed cycle length is then recalled, and scanning is commenced at that value. The confirmed tachycardia cycle length is also held over in temporary storage in case it is needed at the time that the tachyarrhythmia is pace-terminated.

When the tachyarrhythmia is reverted by pacing, the successful scanning parameter value is stored in the array location indexed by the tachycardia cycle length held over since the confirmation prior to delivery of the successful train. If an older successful scanning parameter happens to be stored in that location, it is overwritten by the newly successful value.

For antitachyarrhythmia pacing algorithms utilizing more than one scanning parameter, the array's storage units may be extended so as to accommodate additional parameters' values in each tachycardia cycle length bin, as will appear in greater detail hereinafter in connection with a discussion of the embodiment of FIG. 7.

Referring to FIG. 5a, if two stored parameter values (e.g., "Sm" and "Sn") are at an equal distance from bin "i", yet in opposite directions. That is, $m - i = i - n$, then the number of scan steps in going from "Sm" to "Sn" is measured, and if this is less than the number of scan steps in going from "Sn" to "Sm", then "Sm" is chosen. If the first measurement is greater than the second measurement, then "Sn" is chosen. It should be noted that scanning steps proceed in a direction from lower numbered bins toward higher numbered bins (i.e., from bin "0" toward bin "255"), and when bin "255" is reached the next scan step is back to bin "0". Assuming that "m"=bin "100", "i"=bin "150" and "n"=bin "200" in FIG. 5a, it will be seen that there are $200 - 100 = 100$ scan steps involved in going from bin "m" to bin "n", and $(255 - 200) + 101 = 156$ scan steps involved in going from bin "n" to bin "m". Accordingly, "Sm" in bin "m" is chosen as the starting point. As is apparent from the example under discussion, if the first selection ("Sm" stored in bin "m") is not successful, continued scanning will by itself lead to the second selection ("Sn" stored in bin "n") more quickly than if the second selection were chosen first. If no filled bins are found in the array, then scanning is commenced at zero.

Referring to FIG. 5b, when the tachyarrhythmia is reverted by pacing, the successful scanning parameter value "Sk" is stored in the array location "k" indexed by the latest reconfirmed tachycardia cycle length. If an older successful scanning parameter happens to be stored in that location, it is overwritten by the newly successful value.

Figure 6:
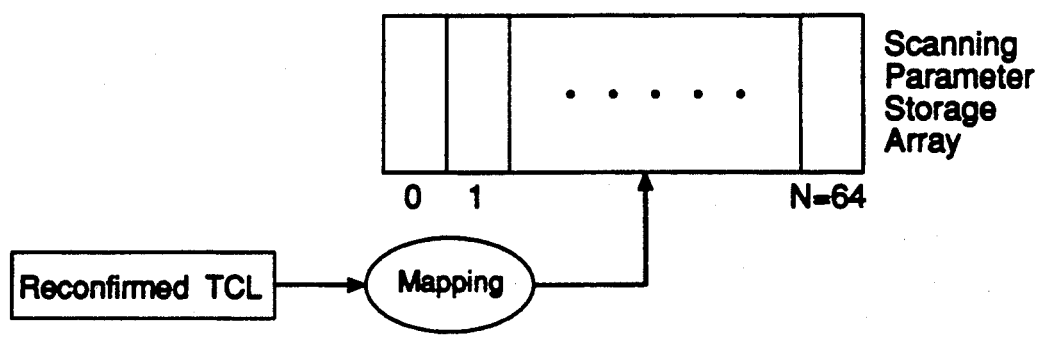
FIG. 6 depicts an alternative embodiment in which fewer bins are used, saving storage space; and, FIG. 7 depicts an alternative embodiment wherein more than one scanning parameter is saved.

FIG. 6 depicts an alternative embodiment of the invention in which fewer bins are used, saving storage space. Where either or both of available storage space and search time are scarce, the number "N" of bins in the scanning parameter storage array can be reduced to less than 256 bins. The reduction in bins is preferably done by dividing the 256 bins of the preferred embodiment by an integral power of 2 to arrive at the number of bins "N" in the smaller array. The arrangement is in general more efficient in either hardware or software if the divisor is an integral power of 2. In the example shown in FIG. 6, a space efficient mapping algorithm is formed by dividing 256 by the divisor 4, resulting in "N"=64. In this case, the reconfirmed tachycardia cycle length does not directly serve as an index into the array but rather must first be mapped onto a set of indices. The simplest such mapping consists of multiplying the reconfirmed TCL by the number (4) used as the divisor to arrive at the number of bins in the smaller array. Accordingly, the embodiment of FIG. 6 provides a scanning parameter storage array which comprises 64 bins which are indexed in increments of 16 milliseconds from 0 to 1008 milliseconds.

Figure 7:
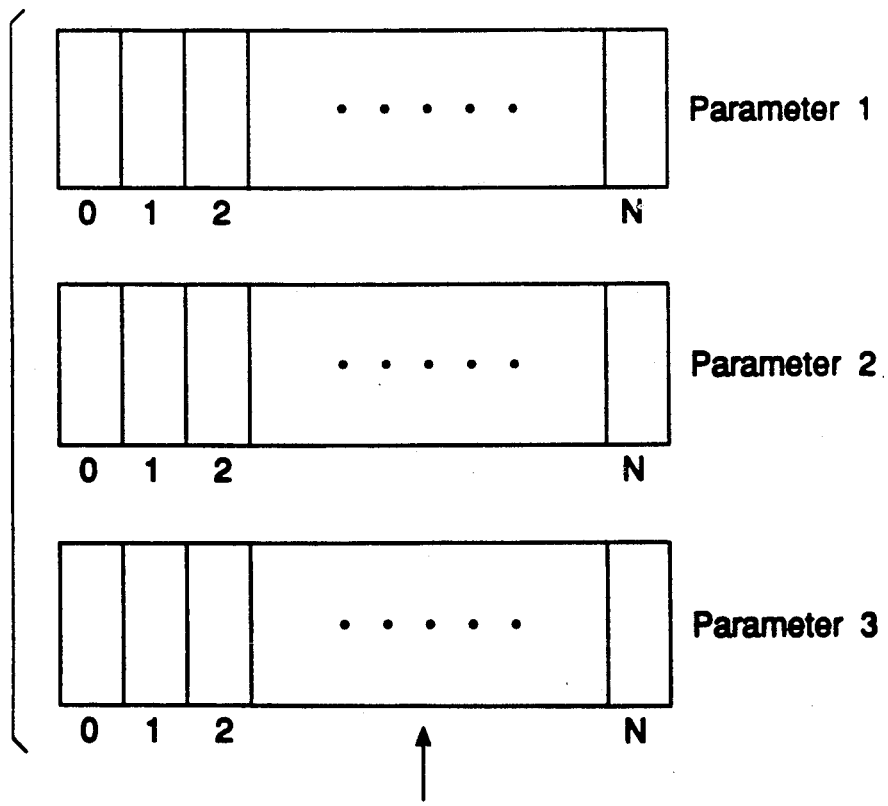

FIG. 7 shows an alternative embodiment wherein more than one scanning parameter is saved. The various scanning parameters are identified in FIG. 7 as Parameters 1, 2 and 3. This figure illustrates the use of the invention's principle in a more complicated antitachycardia pacing algorithm wherein more than one parameter is scanned between pacing trains, the additional parameters being, for example, pulse burst rate and number of pulses. Further details in regard to parameters that may be used for this embodiment of the invention are disclosed in the hereinbefore-mentioned U.S. Pat. No. 4,406,287 to T. A. Nappholz et al. In the present case, one scanning array is allocated for each independent scanning parameter. When the tachyarrhythmia is reverted by pacing, the value of each scanning parameter is stored in its associated array, the location in each array being indexed by the reconfirmed tachycardia cycle length.

Examples of other scanning parameters that may be stored are the initial interval "II" and the coupled interval "CI". The "II" may be scanned as a % of the TCL and/or the CI as a % of the TCL. Preferred examples would be scanning each of these parameters from 90% to 60% of the TCL. Alternately, the "II" and the "CI" may be scanned over an interval ranging from say 460 ms to 200 ms.

An alternative data structure to the scanning parameter storage array described in the preferred embodiment would be a binary tree, or "heap". For a sufficiently large number of bins, a binary tree offers faster "nearest neighbor" searching for accessing the closest previously successful scanning parameter than does the array. However, for a smaller number of bins, the greater storage space requirements of the binary tree method make it less efficient overall than the array method. (For the 256 tachycardia cycle length bins of the preferred embodiment, the array method is more efficient than the binary tree method).

Another alternative data structure would involve dynamic partitioning of the tachycardia cycle length range into a variable number of bins of differing widths. This method has one advantage over the static storage array disclosed in the preferred embodiment, in that the time taken to search for filled bins is always less than the time taken to search the array. However, the storage space required for the dynamic partitioning is equal to or greater than that for the array, and the algorithms to perform the partitioning are more complex than those for maintaining the array. In the preferred embodiment, search time is not critical (for example, the worst case search time is always less than the minimum antitachycardia pacing interval) and so the simpler array method is more appropriate.

Although the invention has been described with reference to particular embodiments, it is to be understood that such embodiments are merely illustrative of the application of the principles of the invention. For example, the principle of the invention applies equally to atrial and ventricular antitachycardia pacing, either with or without defibrillation therapy backup. Furthermore, the parameters which may be incorporated in the invention are not limited to those disclosed herein either directly or by cross reference. Hence numerous other modifications may be made therein and other arrangements may be devised without departing from the true spirit and scope of the invention.

What is claimed is:

1. A method of treating tachycardias comprising the steps of:
   A) selecting a range of tachycardia cycle lengths for which antitachycardia pacing treatment is desired;
   B) selecting a plurality of sub-ranges of tachycardia cycle lengths from said range of tachycardia cycle lengths;
   C) providing a plurality of storage locations corresponding to said tachycardia cycle length sub-ranges;
   D) storing, in corresponding ones of said storage locations, corresponding antitachycardia pacing parameters which have been successful in reverting previous tachycardias having cycle lengths that fall in said corresponding tachycardia cycle length sub-ranges; and,
   E) treating subsequent tachycardias using antitachycardia pacing parameters selected from storage locations that correspond to, or are closest to correspondence with, tachycardia sub-ranges corresponding to the tachycardias to be treated.

2. A method according to claim 1, including the further steps of utilizing a range of antitachycardia pacing parameters in the treatment of tachycardias over a period of time, and correlating successful antitachycardia pacing parameters in such range with the tachycardia cycle lengths of the tachycardias they successfully revert.

3. A method according to claim 2, including the further step of over-riding earlier successful antitachycardia pacing parameters that may be stored in given storage locations with later successful antitachycardia pacing parameters that correspond to such storage locations.

4. A method according to claim 1, wherein said storage locations comprise a first set of storage locations, and wherein said antitachycardia pacing parameters comprise a first set of antitachycardia pacing parameters, and further including the steps of providing a second plurality of storage locations corresponding to said tachycardia cycle length sub-ranges, and storing, in corresponding ones of said second plurality of storage locations, corresponding ones of a second set of antitachycardia pacing parameters which have been used in conjunction with said first set of antitachycardia pacing parameters in successfully reverting previous tachycardias having cycle lengths that fall in said corresponding tachycardia cycle length sub-ranges.

5. A method according to claim 4, including the further steps of utilizing said first and second ranges of antitachycardia pacing parameters in the treatment of tachycardias over a period of time, and correlating successful antitachycardia pacing parameters in such ranges with the tachycardia cycle lengths of the tachycardias they successfully revert.

6. A method according to claim 5, including the further steps of over-riding earlier successful antitachycardia pacing parameters that may be stored in given storage locations in said first and second sets of storage locations with later successful antitachycardia pacing parameters that correspond to such storage locations.

7. A method according to claim 6 further comprising the step of scanning at least said first plurality of storage locations to select a set of antitachycardia pacing parameters for use in reverting said tachycardia, said scanning initiating at a storage location containing a set of antitachycardia pacing parameters and corresponding to a tachycardia cycle length closest to that being treated.

8. A method of claim 7 further comprising the step of initiating scanning at the smaller of $(Sm-Sn) \, \text{Mod}_N$ or $(Sn-Sm) \, \text{Mod}_N$ if said storage location corresponding to said tachycardia being treated contains no such antitachycardia pacing parameters and is located midway between Sm and Sn where Sm and Sn are storage locations that contain antitachycardia pacing parameters, and all storage locations therebetween contain no antitachycardia pacing parameters, N being the total number of storage locations to be scanned.

9. A method of claim 8 further including the step of telemetrically reading at least one of said sets of antitachycardia pacing parameters to determine trends in tachycardia treatment.

10. A method of claim 9 further including the step of overriding a selected storage location and thereby not treating the tachycardia with the parameters stored therein if said selected storage location corresponds to a tachycardia cycle length sub-range that differs by at least a predetermined value from that of the tachycardia being treated.

11. A method according to claim 10 further including the step of varying the predetermined value.

12. A method of claim 11 further comprising the step of telemetrically preloading antitachycardia pacing parameters not yet shown to be successful in treating said tachycardia.

13. Apparatus for treating tachycardias having cycle lengths within a predetermined range of tachycardia cycle lengths, comprising:
  A) means for establishing a plurality of storage locations each of which corresponds to a generally different sub-range of tachycardia cycle lengths within said range of tachycardia cycle lengths;
  B) means for storing, in corresponding ones of said storage locations, corresponding antitachycardia pacing parameters which have been successful in reverting previous tachycardias having cycle lengths that fall in said corresponding tachycardia cycle length sub-ranges; and
  C) means for treating subsequent tachycardias using antitachycardia pacing parameters selected from storage locations that correspond to, or are closest to correspondence with, the tachycardia sub-ranges corresponding to the tachycardias to be treated.

14. Apparatus according to claim 13, further including means for utilizing a range of antitachycardia pacing parameters in the treatment of tachycardias over a period of time, and means for correlating successful antitachycardia pacing parameters in such range with the tachycardia cycle lengths of the tachycardias they successfully revert.

15. Apparatus according to claim 14, further including means for over-riding earlier successful antitachycardia pacing parameters that may be stored in given storage locations with later successful antitachycardia pacing parameters that correspond to such storage locations.

16. Apparatus according to claim 15, wherein said storage locations comprise a first set of storage locations, and wherein said antitachycardia pacing parameters comprise a first set of antitachycardia pacing parameters, and further including means for establishing a second plurality of storage locations corresponding to said tachycardia cycle length sub-ranges, and means for storing, in corresponding ones of said second plurality of storage locations, corresponding ones of a second set of antitachycariia pacing parameters which have been used in conjunction with said first set of antitachycardia pacing parameters in successfully reverting previous tachycardias having cycle lengths that fall in said corresponding tachycardia cycle length sub-ranges.

17. Apparatus according to claim 16, further including means for utilizing first and second ranges of antitachycardia pacing parameters in the treatment of tachycardias over a period of time, and means for correlating successful antitachycardia pacing parameters in such ranges with the tachycardia cycle lengths of the tachycardias they successfully revert.

18. Apparatus according to claim 17, further including means for over-riding earlier successful antitachycardia pacing parameters that may be stored in given storage locations in said first and second sets of storage locations with later successful antitachycardia pacing parameters that correspond to such storage locations.

19. Apparatus according to claim 18 further comprising means for scanning at least said first plurality of storage locations to determine a set of antitachycardia pacing parameters, said scanning initiating at a storage location containing a set of antitachycardia pacing parameters and corresponding to a tachycardia cycle length closest to that being treated.

20. Apparatus of claim 19 further comprising means for initiating scanning at the smaller of $(Sm-Sn)\,Mod_N$ or $(Sn-Sm)\,Mod_N$ if said storage location corresponding to said tachycardia being treated contains no such antitachycardia pacing parameters and is located midway between Sm and Sn, where Sm and Sn are storage locations that contain antitachycardia pacing parameters, and all storage locations therebetween contain no antitachycardia parameters, N being the total number of storage locations to be scanned 21. Apparatus according to claim 20 further including means for telemetrically reading the stored scanning parameters and determining trends in tachycardia treatment therefrom.

22. Apparatus according to claim 21 further including means for overriding a selected storage location and thereby not treating the tachycardia with parameters stored therein if said selected storage location corresponds to a tachycardia cycle length sub-range that differs by at least a predetermined value from the tachycardia being treated.

23. Apparatus according to claim 22 further including means for varying the predetermined value.

* * * * *

UNITED STATES PATENT AND TRADEMARK OFFICE
CERTIFICATE OF CORRECTION

PATENT NO. : 5,144,947

DATED : September 8, 1992

INVENTOR(S) : Stephen G. Wilson

Figure 5C:
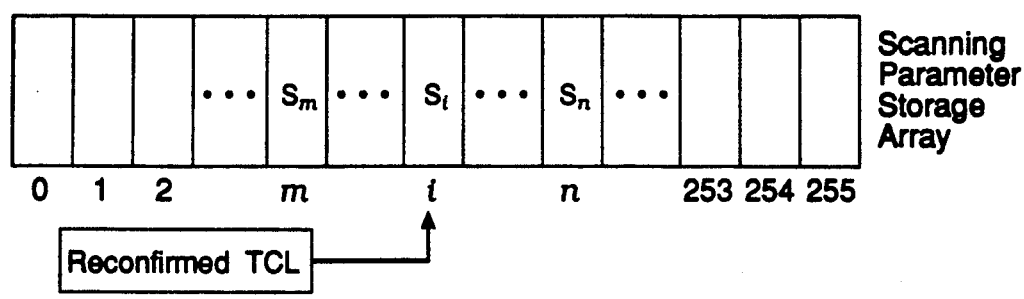
FIG. 5a depicts a preferred embodiment of the invention, in illustrative format, showing the recalling of a stored scan when a cycle length bin is empty but lies between two filled bins and the system searches for that one of such two bins which requires the fewest scan steps to be reached.
FIG. 5b depicts a preferred embodiment of the invention, in illustrative format, showing the storing of a successful scan.
Figure 5D:
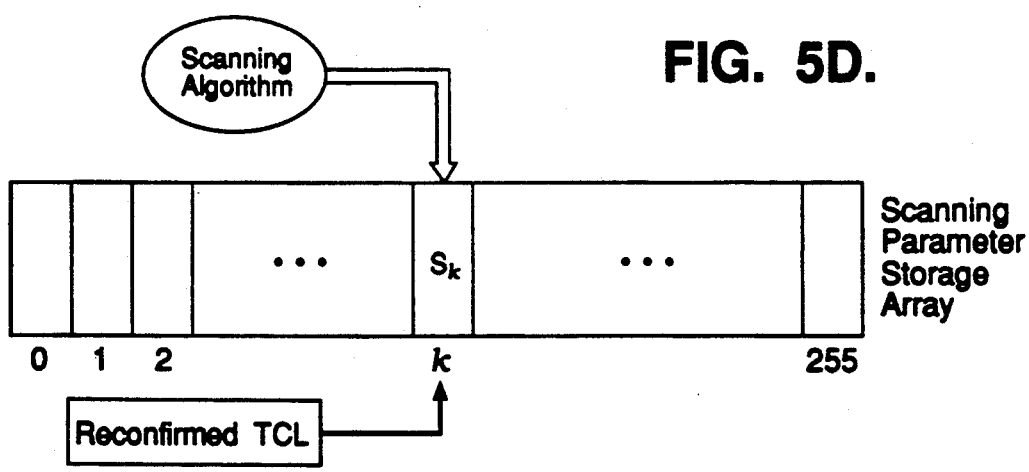

It is certified that error appears in the above-identified patent and that said Letters Patent is hereby corrected as shown below:

IN THE DRAWINGS:

-- FIG. 5C -- Should read -- FIG. 5A --
-- FIG. 5D -- Should read -- FIG. 5B --

Signed and Sealed this

Fifth Day of October, 1993

Attest:

BRUCE LEHMAN

Attesting Officer

Commissioner of Patents and Trademarks